United States Patent [19]

Kissener et al.

[11] Patent Number: 4,820,871

[45] Date of Patent: Apr. 11, 1989

[54] PROCESS FOR THE PREPARATION OF N,N-DIARYL-UREAS

[75] Inventors: Wolfram Kissener, Bergisch Gladbach; Joachim Franke, Cologne; Helmut Fiege, Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 105,856

[22] Filed: Oct. 7, 1987

[30] Foreign Application Priority Data

Oct. 24, 1986 [DE] Fed. Rep. of Germany ....... 3636190

[51] Int. Cl.$^4$ ............................................. C07C 127/19
[52] U.S. Cl. ......................................... 564/55; 564/48; 564/50; 564/52; 564/53; 564/54
[58] Field of Search ....................... 564/50, 52, 53, 54, 564/55, 48

[56] References Cited

U.S. PATENT DOCUMENTS

| 2,683,727 | 7/1954 | Mastin et al. | 560/336 |
| 3,772,372 | 11/1973 | Klauke et al. | 564/54 |
| 4,405,644 | 9/1983 | Kabbe et al. | 564/52 |
| 4,410,697 | 10/1983 | Török et al. | 564/54 |
| 4,473,579 | 9/1984 | Dexries et al. | 564/54 |

FOREIGN PATENT DOCUMENTS 0066922 12/1982 European Pat. Off. .

OTHER PUBLICATIONS

Houben-Weyl, Band E4, 1983, Georg Thieme Verlag, Stuttgart, Seite 182, Absatz 2 in Verbindung mit Seite 353, Absatz 1.

Primary Examiner—Paul Lieberman
Assistant Examiner—Helene Kirschner
Attorney, Agent, or Firm—Sprung Horn Kramer & Woods

[57] ABSTRACT

N,N-Diaryl-ureas of the formula $$R^1-NR^2-CO-NH-R^3$$

wherein
$R^1$ and $R^2$ denote aryl and
$R^3$ denotes alkyl, aralkyl or aryl, can be prepared by a process in which a diarylamine of the formula $$R^1-NH-R^2$$

is reacted with an isocyanate of the formula $$R^3-NCO$$

wherein $R^1$, $R^2$ and $R^{34}$ have the above meaning, in the presence of acid compounds and in the presence or absence of an inert solvent and/or diluent at elevated temperature.

10 Claims, No Drawings

PROCESS FOR THE PREPARATION OF N,N-DIARYL-UREAS

BACKGROUND OF THE INVENTION

The invention relates to a process for the preparation of N,N-diaryl-ureas by reaction of a diarylamine with an isocyanate in the presence of acid compounds.

The preparation of symmetric and unsymmetric ureas by reaction of amines with isocyanates is already known (Houben-Weyl, Methoden der organischen Chemie (Methods of Organic Chemistry), Volume VIII (1952), page 157). If necessary, this reaction is carried out in the presence of basic catalysts. In the case of reactions which proceed with difficulty, for example with sterically hindered amines or those of low nucleophilicity, such as diarylamines, drastic reaction conditions, such as extremely long reaction times, high reaction temperatures or large excesses of isocyanate, are necessary even in the presence of such basic catalysts. Side reactions cannot be excluded with such intensified reaction conditions; for example, the trimerization of the methyl isocyanate which occurs in the presence of basic catalysts greatly reduces the yield of desired urea. It is furthermore known (Chem. Ber. 115 (1982), page 919; and Chem. Ber. 117, (1984), page 1707) that reaction of the diarylamines of low reactivity is successful with isocyanates which have a strongly electron-withdrawing group, for example with $(CF_3CO)NCO$ or $SF_5$—NCO. Such isocyanates are difficult to handle technically and the electron-withdrawing groups mentioned cannot subsequently be replaced by other desired substituents.

SUMMARY OF THE INVENTION

A process for the preparation of N,N-diarylureas of the formula $$R^1-NR^2-CO-NH-R^3$$

in which $R^1$ and $R^2$ are independent of one another and denote aryl and $R^3$ denotes alkyl, aralkyl or aryl, has now been found, which is characterized in that a diarylamine of the formula $$R^1-NH-R^2$$

is reacted with an isocyanate of the formula $$R^3-NCO$$

wherein $R^1$, $R^2$ and $R^3$ have the above meaning, in the presence of acid compounds and the presence or absence of an inert solvent and/or diluent and elevated temperature.

DETAILED DESCRIPTION OF THE INVENTION

Aryl is mononuclear or polynuclear aryl, such as phenyl, naphthyl or anthryl, preferably phenyl or naphthyl. The aryl mentioned can be unsubstituted or substituted; possible substituents are 1 to 3, preferably 1 or 2, substituents, particularly preferably 1 substituent, from the group comprising lower alkyl groups with 1 to 4 C atoms (methyl, ethyl, propyl, isopropyl, butyl and isobutyl), lower alkoxy groups with 1 to 4 C atoms (methoxy, ethoxy, propoxy, isopropoxy, butoxy and isobutoxy) and the halogens (fluorine, chlorine and bromine).

Other substituents can be: the nitro group, the nitrosyl group and the acetyl group.

Alkyl is a straight-chain or branched saturated hydrocarbon radical with 1–12 C atoms, preferably 1–8 C atoms and particularly preferably 1–4 C atoms, such as methyl, ethyl, propyl, isopropyl, butyl, isobutyl, hexyl, octyl or dodecyl. Such hydrocarbon radical can furthermore be mono- or polysubstituted by halogen (fluorine, chlorine or bromine). Examples of such halogenoalkyl radicals are trifluoromethyl, trichloromethyl, tribromomethyl and completely or partly fluorinated, chlorinated or brominated ethyl, propyl, butyl, hexyl, octyl and dodecyl.

Examples of aralkyl which may be mentioned are benzyl, phenyl-ethyl, phenyl-propyl, naphthyl(1- or 2-)-methyl, naphthyl-ethyl or homologues thereof. The aromatic nuclei in the aralkyl groups can carry the same substituents as have been mentioned for aryl.

Preferred diarylamines for the process according to the invention are those of the formula $$R^{11}-NH-R^{12}$$

wherein $R^{11}$ and $R^{12}$ are independent of one another and denote phenyl, naphthyl, $C_1$ to $C_4$-alkylphenyl or $C_1$ to $C_4$-alkylnaphthyl.

Particularly preferred diarylamines for the process according to the invention are those of the formula $$R^{21}-NH-R^{22}$$

wherein $R^{21}$ and $R^{22}$ denote phenyl.

Examples of diarylamines which can be used according to the invention are: diphenylamine, phenylnaphthylamine and ditolylamine, preferably diphenylamine.

Preferred isocyanates for the process according to the invention are those of the formula $$R^{13}-NCO$$

wherein $R^{13}$ denotes $C_1$ to $C_8$-alkyl, phenyl, naphthyl, $C_1$ to $C_4$-alkylphenyl or halogenophenyl.

Particularly preferred isocyanates for the process according to the invention are those of the formula $$R^{23}-NCO$$

wherein $R^{23}$ denotes methyl, ethyl, propyl, butyl, isobutyl, phenyl, chlorophenyl or tolyl.

Examples of isocyanates which can be used according to the invention are: methyl isocyanate, butyl isocyanate and phenyl isocyanate, preferably methyl isocyanate.

The process according to the invention is carried out in the presence of one or more acid compounds. Acid compounds which are used in the process according to the invention are those which are counted as the so-called Bronsted type (that is to say a compound which can split off a proton). The acid compounds can be inorganic or organic in nature. Possible acid compounds for the process according to the invention are accordingly classes of compounds such as the following:

(a) inorganic acids, such as phosphoric acid;

(b) partly esterified polybasic acids which thus still contain an acid group, such as monoalkyl esters of sulphuric acid or mono- or dialkyl esters of phosphoric acid, the alkyl group containing 1 to 8 atoms, preferably 1 to 4 C atoms;

(c) aliphatic, aromatic or heterocyclic mono- or polycarboxylic acids;
(d) partial esters of organic polycarboxylic acids;
(e) aliphatic or aromatic sulphoric acids or phosphonic acids;
(f) acid ion exchanger resins.

Examples which may be mentioned of those acid compounds which can be used according to the invention are: $H_3PO_4$, n-butyl phosphate, di-n-butyl phosphate, acetic acid, propionic acid, benzoic acid, methanesulphonic cid, p-toluenesulphonic acid and others.

Acid compounds which are preferably used in the process according to the invention are: di-n-butyl phosphate, acetic acid, benzoic acid and p-toluene-sulphonic acid.

After the reaction products have been separated off, the acid compounds mentioned can be recycled to another reaction batch of the process according to the invention, if appropriate is a mixture with unreacted starting substances and if appropriate as a mixture with a solvent of diluent. This recycling can also be carried out several times.

Possible solvents or diluents are inert liquids which do not react with the participants in the reaction, for example aliphatic or aromatic hydrocarbons or aliphatic or aromatic halogeno-hydrocarbons.

Examples of suitable solvents and/or diluents are: toluene, xylene, diethyl ether and chloroform.

0,8 to 2 moles, preferably 0,9 to 1,5 moles and particularly preferably 1,0 to 1,2 moles of isocyanate are employed per mole of diarylamine for the process according to the invention.

0,001 to 0,3 moles, preferably 0,002 to 0,1 moles and particularly preferably 0,003 to 0,08 moles of the acid compound are employed per mole of diarylamine for the process according to the invention.

The solvent or diluent or a mixture of several solvents of diluents is employed in an amount of 50 to 2,000, preferably 100 to 1,000 and particularly preferably 200 to 600 millilitres per mole of diarylamine.

The process according to the invention is carried out at elevated temperature, for example at 40° to 160° C., preferably 80° to 140° C. and particularly preferably 90° to 130° C.

The process according to the invention, and in particular the sequence of addition of the reaction partners, can be carried out by various variants. Thus, for example, the diarylamine can be taken together with the isocyanate and the acid compound in an inert solvent or diluent, after which the reaction mixture is brought to the chosen reaction temperature, with stirring. If the chosen reaction temperature is above the boiling point of the solvent or diluent, the reaction can be carried out under increased pressure in a manner known to the expert. Otherwise, the process according to he invention is independent of pressure. In many cases, the urea precipitates out during the reaction or after cooling to room temperature and can thus be isolated in a simple manner. As well as in the manner described, however, the addition of the acid compound can also be carried out so that it is added with one of the reaction compounds or initially introduced in part and added in part. It can thus be advantageous for the acid compound to be taken with one reaction component and the solvent or diluent and for the other reaction component to be added in portions. It is furthermore possible for one reaction component to be taken in the solvent or diluent and for the acid compound to be metered in together with the other reaction component. This metering in can be carried out before, during or after heating to the reaction temperature.

It is furthermore in principle possible, in the case of reaction mixtures which are liquid even without a solvent or diluent, for this solvent or diluent to be dispensed with. However, it is preferable to use a solvent or diluent within the limits of the mounts mentioned above.

According to the invention, it is possible to add acid compounds without impairing the diarylamine employed or the isocyanate employed. This enables the reaction times to be substantially shortened and the reaction temperature to be substantially reduced for the reaction of the diarylamines, which are otherwise only slow to react, with isocyanates. Under these milder conditions, considerably better space/time yields are achieved.

It is particularly surprising that such good space/time yields of N,N-diarylureas are achieved with the process according to the invention, since it is known, for example from Houben-Weyl, Methoden der organischen Chemie (Methods of Organic Chemistry), Volume VIII, page 129 (1952), and from Becker, Braun, Kunststoff-Handbuch, 7 Polyurethane (Plastics Handbook, 7 Polyurethanes), Carl Hanser Verlag, Munich/Vienna, page 8 (1983), that compounds with acid properties, for example hydrogen chloride, acetyl chloride, phosphorus pentachloride and other mineral acids, have the effect of delaying the reaction of isocyanates with compounds with active hydrogen atoms, such as amines. It therefore had to be expected that the acid compounds employed according to the invention would delay the reaction and the space/time yield would thus be reduced.

The N,N-diaryl-ureas which can be prepared according to the invention are used as stabilizers (for example Akardit II ®) or as herbicides in plant protection.

EXAMPLES 1 TO 5

0.5 moles of diphenylamine was taken in 150 ml of toluene. 0.53 mole of methyl isocyanate and 1 g of acid compound (see Table 1) were added. The mixture was heated at 100° C. for 8 hours, with stirring, and allowed to cool to room temperature, and the N-methyl-N', N'-dipenylurea formed was filtered off. The urea was washed with 100 ml of cold toluene. For the yield, see Table 1.

TABLE 1

Dependence of the yield of N—methyl-N',N'—dimethylurea on the catalyst used

| Example | Catalyst | Yield (based on diphenylamine) |
|---|---|---|
| 1 | di-n-butyl phosphate | 95% |
| 2 | acetic acid | 90% |
| 3 | benzoic acid | 95% |
| 4 | methanesulphonic acid | 94% |
| 5 | p-toluenesulphonic acid | 95% |

EXAMPLE 6 (Comparison Example)

The reaction described under Example 1 to give N-methyl-N', N'-diphenylurea without the addition of an acid compound under otherwise identical conditions required a reaction time of 3 days in order to achieve a yield of 85% (based on diphenylamine).

EXAMPLE 7

0.5 mole of α-naphthyl-phenylamine was taken together with 0.53 mole of methyl isocyanate and 0.6 g of di-n-butyl phosphate in 150 ml of toluene. The mixture was warmed at 100° C. for 24 hours, with stirring, and then cooled to 10° C. After the product had been filtered off, washed with 150 ml of cold toluene and dried, 0.4 mole of N-methyl-N'-phenyl-N'-α-naphthyl-urea was obtained. Melting point: 146° C./yield: 80% of theory,

EXAMPLE 8

0,5 mole of diphenylamine was taken together with 0.53 mole of phenyl isocyanate and 0.6 g of di-n-butl phosphate in 150 ml of toluene. The mixture was heated at 100° C. for 24 hours, with stirring, and then cooled to room temperature. At about 30° C., the urea started to crystallize out. After filtering off, washing with 150 ml of cold toluene and drying, 0.41 mole of N-phenyl-N',N'-diphenylurea was obtained. Melting point: 131° C./yield: 82% of theory.

EXAMPLE 9

0.5 mole of diphenylamine was taken together with 0.53 mole of n-butyl isocyanate and 1 g of di-n-butyl phosphate in 150 ml of xylene. The mixture was heated at 120° C. for 24 hours, with stirring, and then cooled to room temperature. After the product had been filtered off, washed with 100 ml of cold xylene and dried, 0.3 mole of N-n-butyl-N',N'-diphenylurea was obtained. Melting point: 92° C./yield: 60% of theory.

EXAMPLE 10

0.5 mole of diphenylamine was taken together with 0.53 mole of methyl isocyanate and 0,6 g of di-n-butyl phosphate in 150 ml of toluene. The mixture was heated at 100° C. for 10 hours, with stirring. After cooling to room temperature, the N-methyl-N',N'-diphenylurea formed was filtered off wtih suction. The filtrate was made up to 150 ml with toluene, and 0.5 mole of diphenylamine and 0.53 mole of methyl isocyanate were added. The mixture was heated again at 100° C. for 10 hours, with stirring, and then cooled to room temperature. Recycling of the filtrate and subsequent addition of in each case 0.5 mole of diphenylamine and 0.53 mole of methyl isocyanate was repeated a further three times. After these five reactions with only a single addition of catalyst, 2.4 moles of N-methyl-N',N'-diphenylurea were obtained. The urea was washed with in each case 100 ml of cold toluene after each reaction. Melting point: 170°/yield: 96% of theory.

It will be appreciated that the instant specification and claims are set forth by way of illustration and not limitation, and that various modifications and changes may be made without departure from the spirit and scope of the present invention.

What is claimed is:

1. A process for the preparation of N,N-diaryl-ureas of the formula $$R^1-NR^2-CO-NH-R^3$$

in which
R$^1$ and R$^2$ are independent of one another and denote aryl and
R$^3$ denotes alkyl, aralkyl or aryl, characterized in that a diarylamine of the formula $$R^2-NH-R^2$$

is reacted with an isocyanate of the formula $$R^3-NCO$$

wherein R$^1$, R$^2$ and R$^3$ have the above meaning, in the presence of inorganic and organic Bronstedt acid compounds and in the presence or absence of an inert solvent, diluent or mixtures thereof, at an elevated temperature wherein 0.001 to 0.3 moles of the acid compound are employed per mole of the diarylamine.

2. A process according to claim 1, characterized in that a diarylamine of the formula $$R^{11}-NH-R^{12}$$

wherein R$^1$ and R$^{12}$ are independent of one another and denote phenyl, naphthyl, C$_1$ to C$_4$-alkylphenyl or C$_1$ to C$_4$-alkylnaphthyl, is employed.

3. A process according to claim 2, characterized in that a diarylamine of the formula $$R^{21}-NH-R^{22}$$

wherein R$^{21}$ and R$^{22}$ denote phenyl, is employed.

4. A process according to claim 1, characterized in that an isocyanate of the formula $$R^{13}-NCO$$

wherein R$^{13}$ denotes C$_1$ to C$_8$-alkyl, phenyl, naphthyl, C$_1$to C$_4$-phenyl or halogenophenyl, is employed.

5. A process according to claim 4, characterized in that an isocyanate of the formula $$R^{23}-NCO$$

wherein R$^{23}$ denotes methyl, ethyl, propyl, butyl, isobutyl, phenyl, chlorophenyl or tolyl, is employed.

6. A process according to claim 1, characterized in that 0.8 to 2 moles of the isocyanate are employed per mole of the diarylamine.

7. A process according to claim 6, characterized in that 0.9 to 1,5 moles of the isocyanate are employed per mole of the diarylamine.

8. A process according to claim 7, characterized in that 1.0 to 1.2 moles of the isocyanate are employed per mole of the diarylamine.

9. A process according to claim 1, characterized in that 0.002 to 0.1 moles of the acid compound are employed per mole of the diarylamine.

10. A process according to claim 9, characterized in that 0.003 to 0.08 moles of the acid compound are employed per mole of the diarylamine.

* * * * *

UNITED STATES PATENT AND TRADEMARK OFFICE
CERTIFICATE OF CORRECTION

PATENT NO. : 4,820,871

DATED : April 11, 1989

INVENTOR(S) : Kissener et al

It is certified that error appears in the above-identified patent and that said Letters Patent is hereby corrected as shown below:

Col. 6, line 8       Delete 1st "$R^2$" and substitute —$R^1$—

Signed and Sealed this

Sixteenth Day of January, 1990

*Attest:*

JEFFREY M. SAMUELS

*Attesting Officer*   *Acting Commissioner of Patents and Trademarks*